US008980310B2

(12) United States Patent
Daftary et al.

(10) Patent No.: US 8,980,310 B2
(45) Date of Patent: Mar. 17, 2015

(54) NON-PEGYLATED LONG-CIRCULATING LIPOSOMES

(75) Inventors: Gautam Vinod Daftary, Thane (IN); Srikanth Annappa Pai, Thane (IN); Sangeeta Hanurmesh Rivankar, Thane (IN)

(73) Assignee: Bharat Serums and Vaccines, Ltd., Thane (IN)

(*) Notice: Subject to any disclaimer, the term of this patent is extended or adjusted under 35 U.S.C. 154(b) by 1345 days.

(21) Appl. No.: 10/748,094

(22) Filed: Dec. 31, 2003

(65) Prior Publication Data
US 2005/0142178 A1 Jun. 30, 2005

(30) Foreign Application Priority Data
Dec. 31, 2002 (IN) ............... 1101/MUM/02

(51) Int. Cl.
*A61K 9/127* (2006.01)
*A61K 31/704* (2006.01)

(52) U.S. Cl.
CPC ............... *A61K 31/704* (2013.01); *A61K 9/127* (2013.01)
USPC ........................................... 424/450; 264/4.1

(58) Field of Classification Search
CPC ...................................................... A61K 9/127
USPC ........................................... 424/450; 264/4.1
See application file for complete search history.

(56) References Cited

U.S. PATENT DOCUMENTS

| | | | | |
|---|---|---|---|---|
| 4,235,871 A * | 11/1980 | Papahadjopoulos et al. | . | 424/450 |
| 4,501,728 A | 2/1985 | Geho et al. | | |
| 4,769,250 A | 9/1988 | Forssen | | |
| 4,880,635 A | 11/1989 | Janoff et al. | | |
| 4,920,016 A | 4/1990 | Allen et al. | | |
| 5,013,556 A | 5/1991 | Woodle et al. | | |
| 5,192,528 A * | 3/1993 | Radhakrishnan et al. | ...... | 424/45 |
| 5,316,771 A * | 5/1994 | Barenholz et al. | ............ | 424/450 |
| 5,676,971 A | 10/1997 | Yoshioka et al. | | |
| 5,714,163 A * | 2/1998 | Forssen et al. | ................ | 424/450 |
| 5,756,122 A | 5/1998 | Thierry et al. | | |
| 5,939,096 A * | 8/1999 | Clerc et al. | .................... | 424/450 |
| 6,083,530 A | 7/2000 | Mayer et al. | | |
| 6,110,491 A * | 8/2000 | Kirpotin | ....................... | 424/450 |
| 6,132,763 A | 10/2000 | Fisher | | |
| 6,355,268 B1 * | 3/2002 | Slater et al. | ................... | 424/450 |
| 6,627,623 B2 | 9/2003 | Ho et al. | | |
| 6,638,504 B1 | 10/2003 | Lukanidin | | |
| 2002/0151508 A1 * | 10/2002 | Emanuel et al. | ................ | 514/34 |
| 2002/0172711 A1 * | 11/2002 | Martin et al. | ................. | 424/450 |
| 2003/0129223 A1 * | 7/2003 | Wartchow et al. | ........... | 424/450 |
| 2003/0228355 A1 * | 12/2003 | Zarif et al. | .................... | 424/450 |
| 2004/0258747 A1 * | 12/2004 | Ponzoni et al. | ............... | 424/450 |
| 2005/0025822 A1 * | 2/2005 | Wong et al. | ................... | 424/450 |
| 2005/0129750 A1 * | 6/2005 | Hu et al. | ....................... | 424/450 |
| 2006/0078605 A1 * | 4/2006 | Mammarella | ................ | 424/450 |

FOREIGN PATENT DOCUMENTS

EP 0 561 424 81 3/1997

OTHER PUBLICATIONS

Park et al. Biochimica Biophysica Acta, 1108, p. 257-260, 1992.*
Maruyama International Journal of Pharmaceutics, 111, p. 103-107, 1994.*
Uchiyama International Journal of Pharmaceutics, 121, p. 195-203, 1995.*
Kenneth B. Gordon, "Cancer", *Hand-Foot Syndrome Associated with Liposome-Encapsulated Doxorubicin Therapy*, vol. 75, No. 8. pp. 2169-2173, (1995).
Ruey-Long Hong, et al., "Clinical Cancer Research", *Direct Comparison of Liposomal Doxorubicin with or without Polyethylene Glycol Coating in C-26 Tumor-bearing Mice: Is Surface Coelho with Polyethylene Glycol Beneficial*, vol. 5, pp. 3645-3652, (1999).
Alberto A. Gabizon, M.D., Ph.D., "Cancer Investigation" *Pegylated Liposomal Doxorubicin: Metamorphosis of an Old Drug into a New Form of Chemotherapy*, vol. 19, No. 4, pp. 424-436, (2001).

* cited by examiner

*Primary Examiner* — Gollamudi Kishore
(74) *Attorney, Agent, or Firm* — Hogan Lovells US LLP

(57) ABSTRACT

The present invention provides a long circulating non-pegylated liposomal doxorubicin hydrochloride composition for parenteral administration and a process for its preparation. The circulation time in Swiss albino mice is at least 25 times longer than conventional non-liposomal formulations. The non-pegylated liposomes are stable, exhibit low toxicity and have been found to be efficacious in different tumor models.

26 Claims, No Drawings

NON-PEGYLATED LONG-CIRCULATING LIPOSOMES

This application claims priority to provisional application 1101/Mum/02, filed on Dec. 31, 2002 which is hereby incorporated by reference in its entirety. This application is related to PCT application number PCT/IN2003/000424, filed on Dec. 31, 2003, entitled "NON-PEGYLATED LONG-CIRCULATING LIPOSOMES" which contains subject matter related to the subject matter of the present patent application and which is incorporated herein by reference in its entirety.

FIELD OF THE INVENTION

The present invention relates to non-pegylated, long circulating liposomes for parenteral administration and the manufacture thereof, that can be used to contain and deliver diagnostic or therapeutic agents.

BACKGROUND OF THE INVENTION

Liposomes are commonly composed of phospholipid and/or sterols and consist of a vesicular structure based on lipid bilayers surrounding aqueous compartments. They vary widely in their physicochemical properties such as size, surface charge, and phospholipid composition.

Liposomes have received increasing attention as possible carriers for diagnostic or therapeutic agents. For example, liposomes have been used to deliver diagnostic agents such as contrast agents for magnetic imaging such as Gd:diethylenetriaminepentacedic acid chelate (Gd-DTPA) (See e.g. U.S. Pat. No. 6,132,763) and therapeutic agents such as anthracycline agents, which have been shown to exhibit marked activity against a wide variety of neoplasms. (See e.g. U.S. Pat. No. 4,769,250).

However, liposomes cause aggregation in the blood by their mutual reaction with various blood plasma proteins and are captured by the reticuloendothelial system (RES). For example, Kupfer cells in the liver or fixed macrophages in the spleen take up the liposomes before they can reach their intended target. Capture by the RES has rendered selected delivery of the liposomes to target tissues or cells very difficult.

In addition to capture by the RES, the liposomes are subject to electrostatic, hydrophobic, and Van der Waals interactions with plasma proteins. These interactions result in destabilization of the liposomes leading to rapid clearance of the vesicles from circulation, often before reaching their target.

Also, in addition to cellular and protein interactions with the liposomes, difficulties have arisen in producing liposome encapsulating certain drugs because of the drugs' interactions with the phospholipids of the liposomes. For example, anthracyclines have exhibited a surfactant or detergent-like effect on the phospholipid vesicle bilayer that causes leakage and creates liposome vesicle instability. Thus, liposomes unstable to the circulation environment and/or its content will leak the antineoplastic agent prematurely before reaching the tumor site. As a result of the "leaky" liposomes and the resulting devastating toxicities, scientists have tried to develop long-circulating liposomes that are able to extravasate to tumor sites, which are highly vascular in nature.

Since most commonly used anti-cancer drugs are not specifically toxic to tumor cells and are toxic to all tissues they contact, they create undesirable side effects as a result of their interactions with normal tissues. For example, Doxorubicin hydrochloride is one of the most commonly used cytotoxic anthracycline antibiotics used in cancer chemotherapy and has been shown to have activity against a wide variety of neoplasms. Doxorubicin hydrochloride is effective in the treatment of many solid tumors and leukemias. It is particularly effective in the treatment of breast cancers involving polytherapies. Doxorubicin hydrochloride is protocol therapy for AIDS related Kaposi's sarcoma. Doxorubicin hydrochloride also has notable activity against tumors of the ovaries, lung, testes, prostate, cervix, head and neck, oestrogenic sarcomas and Ewing's sarcoma.

Conventional compositions of Doxorubicin hydrochloride are available as freeze-dried product or as a solution of Doxorubicin hydrochloride in water. Freeze-dried product requires reconstitution with Water for Injection before administration. Both these marketed products have been associated with a number of toxicities when administered intravenously. Severe myelosuppression is usually the dose limiting factor. Other toxicities include nausea and vomiting, alopecia, mucositis (including stomatitis and esophagitis) and cardiotoxicity, which may limit Doxorubicin hydrochloride use. Doxorubicin hydrochloride is a potent vesicant that may cause extravasation and necrosis at the injection site or at any site that the skin is exposed. "Doxorubicin flare" is not uncommon and is characterized by erythematous streaking at the injection site. "Doxorubicin flare" usually subsides in about a half an hour.

The mechanism of action of Doxorubicin hydrochloride is not known exactly but many possibilities have been studied and described. The primary mechanism involves the ability of Doxorubicin hydrochloride to intercalate DNA. The integrity of the DNA is significantly compromised and commonly results in altered DNA functions. Single and double strand brakes are also common due to Doxorubicin hydrochloride intercalation with DNA. Another mechanism of Doxorubicin hydrochloride involves its ability to generate free radicals that induce DNA and cell membrane damage. Doxorubicin hydrochloride also inhibits topoisomerase II, rendering the reproduction of DNA ineffective.

Some of the resulting toxic affects of Doxorubicin hydrochloride include cardiac toxicity, anaphylactic reaction, emetogenicity, myelosuppression, muccocytis, skin toxicity, alopecia, and toxicity to the injection sight. (*Cancer Investigation,* 19 (4): 424-436 (2001)). In theory, prolonged circulation systems (slow release) that effectively deliver and release a drug to tumors and the near vicinity of tumor cells are more advantageous. Thus, it is desirable to have a stable liposome capable of encapsulating agents, such as Doxorubicin hydrochloride, that do not prematurely release their contents to healthy or non-cancerous tissues.

Several approaches taken in an effort to increase the circulation time of liposomes and thus ensure delivery of the liposome contents to the target tissue include the following: masking the liposomes from the reticuloendothelial system recognition using a sialic acid residue coating (U.S. Pat. No. 4,501,728); rigidifying the liposome membrane with sphingomyelin or neutral phospholipid with predominantly saturated acyl chains containing 5 to 20% glycolipid (U.S. Pat. No. 4,920,016); forming liposomes with a 3-80 fold higher drug to lipid ratio than traditional liposome preparations in a 3-compartment system of the agent, bilayers, and release inhibiting buffer containing citric acid (U.S. Pat. No. 6,083,530); incorporating cholesterol in the liposome (Alberto A. Gabizon, *Cancer Investigation,* 19(4) 424-436 (2001)); and derivatizing the phospholipid with polyethylene glycol (pegylated liposomes) (U.S. Pat. Nos. 5,013,556 and 6,132,763).

Unfortunately, the above approaches have shown only limited potential to extend the circulation time of the liposomes in vivo. For example, it has been determined that masking the liposome with sialic acid only had limited ability to extend the circulation half lives of in vivo liposomes. (U.S. Pat. No. 4,920,016). To overcome these problems, scientists have coated the liposome surface with a hydrophilic polymer such as polyethylene glycol (PEG) to prevent adsorption of various blood plasma proteins to the liposome surface. (See e.g. U.S. Pat. Nos. 5,013,556, and 5,676,971). These pegylated liposomes have been called sterically stabilized liposomes or stealth liposomes. The pegylated liposomes appeared to reduce some of the toxic effects caused by the release of their contents, but, unfortunately, new toxic effects appeared because of the presence of the polyethylene glycol. For example, the liposomal preparations containing pegylated phospholipids have lead to skin toxicity generally known as "Hand-Foot syndrome," which results in skin eruptions/ulcers on the palms of the hands and soles of the feet. (Kenneth B. Gordon, *Cancer*, Vol. 75(8), 1995, 2169-2173).

Another disadvantage with pegylated liposomes is the presence of large molecules (PEG) on the liposomal surface may reduce the interactions of liposomes with cells and hinder entry of liposomes into the tumor tissue, thereby possibly reducing the accumulation of liposomal drug in the tumor tissue. (*Clinical Cancer Research*, (5), 1999, 3645-3652)

Thus, there remains a need for stable, long circulating liposomes that do not cause such deleterious effects such as the "Hand-Foot syndrome" as well as methods of manufacturing such liposomes and compositions based on them. The present invention meets this need, as well as provides for methods of treatment of various conditions by administering the liposomes of the present invention.

SUMMARY OF THE INVENTION

The present invention provides a process for the manufacture of long circulating non-pegylated liposomes; the process comprising dissolving one or more phospholipids, a sterol in a solvent or mixture of solvents; removing the said solvents before or after hydrating the lipids by addition of a aqueous hydration media to form non-pegylated liposomes; wherein the amount of the aqueous hydration media used is in the range of 10 to 35 ml for each mmole of phospholipid present in the lipid solution.

Preferably the amount of aqueous hydration media used is 30 ml for each mmole of phospholipid in the lipid solution.

The present invention further provides a process for manufacture of long circulating non-pegylated sized liposomes comprising dissolving one or more phospholipids, and a sterol in a solvent or mixture of solvents; removing said solvents before or after hydrating the phospholipids by addition of an aqueous hydration media to form non-pegylated liposomes; wherein the amount of the aqueous hydration media used is in the range of 10 to 35 ml for each mmole of phospholipid present in the lipid solution; sizing the non-pegylated liposomes to about 0.06 µm to 0.1 6 µm to form a liposomal composition; and removing extra-liposomal hydration salt from the liposomal composition using sucrose-histidine buffer solution to form non-pegylated sized liposomes.

The process of manufacture of the non-pegylated liposomes may further comprise loading the liposomes with a therapeutic or diagnostic agent. Preferably therapeutic agent is an antineoplastic agent such as Doxorubicin hydrochloride, Daunorubicin hydrochloride, and Epirubicin hydrochloride. Doxorubicin hydrochloride is more preferred.

Preferably the molar ratio of phospholipid to sterol is from about 1:0.1-1:2 and is more preferably about 1:0.7

A preferred aqueous hydration media comprises ammonium sulfate and sucrose, and the concentration of ammonium sulfate in the aqueous hydration media is not less than 125 mmoles/liter.

Preferred phospholipids have a phase transition temperature of about 40° C. to 60° C., have a fatty acid chain of a minimum of sixteen carbons and are selected from the group consisting of Distearoyl phosphatidylcholine (DSPC), Dipalmitoyl phosphatidylcholine (DPPC), Hydrogenated soya phosphatidylcholine (HSPC) and derivatives of such phospholipids. A preferred phospholipid is distearoyl phosphatidylcholine (DSPC) and a preferred sterol is cholesterol.

The process may also involve sizing of the non-pegylated liposomes. They are preferably sized by extrusion successively through filters having a pore size of 0.4 µm to 0.05 µm.

Another embodiment of the present invention provides for liposomes obtainable by the process described herein. Liposomes of the present invention have the ingredients in the concentrations and proportions described above in the process for the manufacture thereof and the average size liposomes so obtained is 0.6 µm to 0.16 µm.

The present invention also provides for a long circulating non-pegylated liposomal doxorubicin composition for parenteral administration comprising, doxorubicin non-pegylated liposomes, histidine hydrochloride, and sucrose; wherein the doxorubicin non-pegylated liposomes comprise distearoylphosphatidyl choline, cholesterol, sucrose in addition to doxorubicin hydrochloride; wherein the liposomes have an average size 0.06 µm to 0.160 µm; and wherein the non-pegylated doxorubicin liposomes have a circulation time in blood at least 25 times longer than that obtained with ADRIAMYCIN when tested in Swiss albino mice at equivalent doses.

Doxorubicin hydrochloride concentration encapsulated in the liposomes is from is 1 to 10 mM, and preferably is from 3 mM to 7 mM, more preferably 6.9 mM and most preferably 3.45 mM.

The molar ratio of distearoylphosphatidyl choline to cholesterol is from 1:0.6 to 1:0.8; preferably 1:0.7.

The molar ratio of doxorubicin hydrochloride to distearoylphosphatidyl choline is preferably from 1:2 to 1:15; and more preferably 1:3.5.

The sucrose concentration is preferably from 0.1M to 0.5M, and more preferably from 0.25M to 0.3M.

The concentration of histidine hydrochloride is from 1 mM to 100 mM, preferably from 8 to 12 mM, and more preferably about 10 mM.

The preferred average size of the liposomes is from 0.08 µm to 0.12 µm.

An exemplary composition is the doxorubicin hydrochloride present at 2 mg/ml; and the molar ratio of doxorubicin to phospholipid is about 1:3.5; and the ratio of phospholipid to cholesterol is about 1:0.7.

Another exemplary composition comprises doxorubicin hydrochloride present at 4 mg/ml and the molar ratio of doxorubicin to phospholipid is about 1:3.5 and the ratio of phospholipid to cholesterol is about 1:0.7. The circulation time (t½) of the composition in blood is preferably more than 40 times longer than that obtained with ADRIAMYCIN when tested in Swiss albino mice at equivalent doses.

The present invention also provides a process for manufacture of long-circulating non-pegylated liposomal doxorubicin compositions.

The present invention also methods for reducing tumor growth comprising administering the compositions of the present invention.

DETAILED DESCRIPTION OF THE INVENTION

The present invention provides stable, long circulating, non-pegylated liposomes, as well as a method of manufacture thereof. Pegylated liposomes are liposomes coated with polyethyleneglycol (PEG). The surface of the liposome is decorated with several thousand strands of PEG, a process called "pegylation." The PEG strands make the surface of the liposome "hairy," and this prevents the rapid absorption of liposomes to the surface of blood proteins. The rapid absorption accelerates the rapid removal from blood of liposomes. In contrast, the pegylated liposomes are protected and are removed from blood at a much slower rate. Compared with liposomes made without PEG, pegylated liposomes are more stable and are less extensively taken up by cells of the reticuloendothelial system (RES), and have a reduced tendency to leak any encapsulated agent or drug while in circulation. For example, the pharmacokinetics of PEG-liposomes encapsulating doxorubicin is characterized by a long circulating half-life, slow plasma clearance, and a reduced volume of distribution compared with non-pegylated liposomal doxorubicin or free doxorubicin. The long circulation and ability of pegylated liposomes to extravasate through tumor vasculature results in localization of doxorubicin in tumor tissue with the increased possibility of increased tumor response because of enhanced drug accumulation especially in highly angiogenic tumors. Also, the increased stability of pegylated liposomes over conventional liposomes results in a decrease in availability of drug in the tissue of sensitive organs and thereby a decrease in toxicity and other adverse effects such as nausea, vomiting, and alopecia. A serious side effect known as "Hand-Foot syndrome," however, where skin eruptions or ulcers have been observed on the palms of the hands and soles of the feet, have been reported to result from clinical uses of the pegylated liposomes. (Kenneth B. Gordon, *Cancer*, Vol. 75(8), 1995, 2169-2173). Another disadvantage with pegylated liposomes is the presence of large molecules (PEG) on the liposomal surface may reduce the interactions of liposomes with cells and hinder entry of liposomes into the tumor tissue, thereby possibly reducing the accumulation of liposomal drug in the tumor tissue.

The process of the present invention provides stable, long circulating, low toxicity non-pegylated liposomes that exhibit the stability of the pegylated liposomes with the long circulation half-life and reduced toxicity described above. However, since the liposomes of the present invention do not require the use of PEG to achieve the above results, they do not cause "Hand-Foot syndrome."

In the process of the present invention, hydration of lipids may be carried out before evaporation of the solvent or may be carried out after evaporation of the solvent that is used for dissolving lipids. Solvents suitable to the invention are organic solvents in which the phospholipid can be dissolved. One skilled in the art would appreciate commonly used and suitable solvents in the manufacture of liposomes. Exemplary suitable solvents include but are not limited to chloroform, methylene chloride, ethanol, methanol, acetone.

When the hydration of lipids is carried out after evaporation of the solvent, solvents such as chloroform, methylene chloride are preferred solvents.

When the hydration of lipids is carried out before evaporation of the solvent, water miscible solvents such as ethanol, methanol, acetone are preferred solvents When hydration is carried out after evaporation of the solvent, the process comprises; forming a lipid film by evaporating a solvent from a lipid solution comprising one or more phospholipids, a sterol, and a solvent or a mixture of solvents. Evaporation of a solvent can be accomplished by any evaporative technique such as, but not limited to, evaporation by passing a stream of inert gas over the solution, by heating, by vacuum, or by heating under vacuum. Commonly, rotary evaporator flasks are employed.

When the hydration is carried out before the evaporation of solvent, the process comprises evaporation of the solvent from the aqueous liposomal suspension containing solvent. Evaporation of a solvent can be accomplished by any evaporative technique such as, but not limited to, evaporation by passing a stream of inert gas over the solution, by heating, by vacuum, or by heating under vacuum. Commonly, rotary evaporator flasks are employed. After a solvent or mixture of solvents is evaporated, only the liposomes remain in the aqueous suspension form.

Any phospholipid suitable to prepare liposomes may be used in the present invention. Suitable phospholipids include those that tend to decrease permeability of the liposomal membrane. Liposomes containing phospholipids with long fatty acid chains are more suitable and result in a slower release of agent than liposomes comprised of phospholipids having shorter fatty acid chains. As the carbon chain length of the fatty acid increases, the phase transition temperature also increases. Liposomes comprised of phospholipids with higher phase transition temperature release their contents slower than liposomes comprised of lower phase transition phospholipids. Higher phase transition temperatures enable slow releasing of the contents from inside the liposomes into the blood stream as the phospholipid membranes are semipermeable. Other phospholipid characteristics that effect membrane permeability and stability include degree of saturation and charge.

Preferably, liposomes of the present invention contain neutral lipids. It is preferred that the neutral lipids have a phase transition temperature of 40° C. to 65° C. and more preferably of about 50° C. to 54° C. Preferable phospholipids have a fatty acid chain of at least sixteen carbons.

Suitable phospholipids of the present invention include, but are not limited to, Distearoyl phosphatidylcholine (DSPC), or Dipalmitoyl phosphatidylcholine (DPPC), Hydrogenated soya phosphatidylcholine (HSPC) or derivatives of such phospholipids. Phosphatidylcholines are preferred neutral lipids. A preferred phospholipid is 1,2,-Distearoly-sn-glycerol-3-phosphocholine, which is commonly known as distearoyl phosphatidylcholine (DSPC). The molecular weight of DSPC is 790 and has the molecular formula of $C_{44}H_{88}NO_8P$.

Sterols are incorporated into liposomes along with phospholipids to alter rigidity and permeability of liposome membranes. An exemplary sterol is cholesterol and derivatives or analogs thereof. Cholesterol tends to increase rigidity and decrease permeability of liposomal membranes. Cholesterol is an amphipathic molecule and inserts itself into the phospholipid membrane with its hydroxyl groups orientated towards the aqueous surface. Cholesterol is incorporated in a concentration that provides optimum permeability to the liposome membrane, but also maintains the rigidity of the membrane. The selection of phospholipid to cholesterol ratio defines the rate of dissolution of the contents from the liposomes. Liposomes of the present invention have a molar ratio of phospholipids to sterol ranging from 1:0.1 to 1:2. Preferably the range is from 1:0.5 to 1:1.5. A preferable molar ratio of phospholipids to sterol when distearoly phosphotidyl choline (DSPC) is the phospholipid and cholesterol is the sterol is from 1:0.6 to 1:0.8. A preferred molar ratio is about 1:0.7.

The solvent or mixtures of solvents are evaporated under vacuum. In the process when the hydration is carried out after removing the solvents, the lipid film formed is hydrated with an aqueous hydration media to form liposomes. The aqueous hydration media is added to the film with agitation or under mixing to hydrate the lipid film and form liposomes. One skilled in the art would appreciate suitable aqueous hydration medias to employ. Preferable aqueous hydration medias contain buffers/salts so as to be available to establish a chemical gradient later in the process to assist in loading various agents into the liposomes. Exemplary hydration medias include, but are not limited to, ammonium hydroxide, ammonium sulfate, ammonium carbonate, and ammonium bicarbonate. A preferred aqueous hydration media contains ammonium sulfate. Also, the aqueous hydration media contain an iso-osmotic agent, such as but not limited to sucrose, sodium chloride, dextrose, or mannitol. It is preferable that the iso-osmotic agent is non-reactive with other contents of the solution and the liposomes themselves. The iso-osmotic agent is preferably sucrose since it is least reactive. When the aqueous hydration media contains ammonium sulfate, preferably the iso-osmotic agent is sucrose. Sucrose helps in protecting and rigidifying the liposomal membrane and also to maintain the isotonicity of the liposomal composition.

The volume of the aqueous hydration media is controlled/reduced as compared to amounts of hydration media used in conventional liposome and pegylated liposome manufacture. By reducing the volume of aqueous hydration media, the phospholipids can pack tighter together resulting in a thicker liposome membrane or "shell." The thicker "shell" provides for stable, long-circulating, slow release and decreased toxicity of the liposome contents without the need for PEG. The smaller the volume of hydration media used, the tighter the phospholipids will pack together and the thicker the shell will become. By "controlled/reduced" it is meant that the volume of aqueous hydration media used in the present invention is less than previously known or accepted amounts of aqueous hydration media. Using a preferred reduced volume of hydration media (i.e. 30 ml for each mmole of phospholipid) and a preferred concentration of cholesterol, the resulting liposomal composition would have a rigid phospholipid bilayer.

This reduction in hydration volume can also be viewed in terms of the ratio of volume of buffer used per moles of phospholipid present in the lipid solution. In the present invention, the amount of aqueous hydration media used is in the range of 10 to 35 ml for each mmole of phospholipid present in the lipid solution. Preferably the volume of aqueous hydration media is between 20-30 ml for each mmole of phospholipid present in the lipid solution. More preferably, the volume of aqueous hydration media is 30 ml for each mmole of phospholipid used in the lipid solution.

Liposomes are sized appropriately. One skilled in the art would appreciate known methods of liposome sizing. Homogenization under pressure is one such method. Another suitable method includes extruding the liposomes through filters with a pore size to match the desired liposome size. Because the liposomes of the present invention have a tighter packed membrane, sizing tends to be more difficult than with conventional liposomes. Thus, they are preferably sized through a series of filters with increasingly smaller pore size. For example, following hydration, liposomes are initially passed through a filter having a pore size of 0.40 µm followed by successively smaller pore sized filters of about 0.05 µm. The resulting liposomes have an average size range from 0.06 µm-0.2 µm. A preferred average size range is from 0.08 µm to 0.12 µm.

Extraliposomal salt in the hydration media is removed or washed from the liposomes. Dialysis using a dialysis medium is an exemplary method of removing extraliposomal hydration media salt. Any suitable buffer solution may be used in the dialysis. Removal of extraliposomal salt present in the liposomal composition creates an inside-to-outside chemical gradient across the liposomal membrane, which is later called upon for loading of the liposomes. Other suitable means to remove the extraliposomal salt includes ultrafiltration or column chromatography.

The liposomes of the present invention provide a long circulating, slow release delivery mechanism for therapeutic or diagnostic agents. Any known method can be used to load the liposomes with a desired therapeutic or diagnostic agent. Exemplary methods include adding the agent to the lipid film before hydration of the lipid film, incorporating the agent directly into the hydration media, by pH gradient, or by chemical gradient. A preferred method involves loading an agent using a chemical gradient. When the liposomes are loaded by active loading process, the drug solution is admixed with the blank liposomal suspension at a temperature higher than or equivalent to phase transition temperature of the phospholipids.

Using a chemical gradient, the amount of agent can be readily controlled and once the agent is loaded inside the liposomes, the leakage into the extraliposomal media is minimal. In addition, if a hydration media containing a buffer/salts is used in the hydration step, the creation of such a gradient becomes very feasible after removing the extraliposomal hydration media salt as described above. One such exemplary hydration media that may be used to create a chemical gradient useful in liposome loading contains ammonium sulfate. However, hydration with Ammonium sulfate solution rendered isotonic with sodium chloride (See U.S. Pat. No. 5,316,771) results in liposomes which leak on storage. The free drug content of the liposomal composition increases on storage, which in turn increases the toxicity. Hence there is a need to strengthen the liposomal membrane. The present invention thus provides the concomitant use of an iso-osmotic agent that is non-reactive with other ingredients of the solution and the liposomes themselves in the hydration media. Preferably the iso-osmotic agent is sucrose. It was found that use of sucrose is protective for liposomal membranes. Sucrose helps in protecting and rigidifying the liposomal membrane and also to maintain the isotonicity of the liposomal composition. Liposomal membranes have been protected for dehydration before freeze drying by use of saccharides such as trehalose, sucrose, maltose (U.S. Pat. No. 4,880,635).

The present invention thus provides using sucrose with ammonium sulfate as a hydration medium giving liposomes that are more rigid and that do not leak the agent encapsulated in them on storage. With the addition of sucrose to the hydration medium, sucrose remains inside and outside surface of the liposomal membrane hardening both sides of the liposomal membrane, thereby reducing the leakage of the drug. It is preferable that the concentration of sucrose in the hydration media is from 0.1M to 0.5M. A concentration of 0.25M to 0.3M is preferred.

The concentration of ammonium sulfate in the hydration media plays a vital role on drug leakage from the liposomes. Ammonium sulfate solution in a concentration less than 125 mM whenever used for hydration for forming liposomes showed the drug leakage on storage. Thus in a preferred method of manufacture, the concentration of ammonium sulfate in hydration media is greater than 125 mM, which in turn produces liposomal compositions with reduced leakage on storage. Thus, in a preferred method the concentration of ammonium sulfate solution is not less than 125 mmole/liter, and the hydration media contains sucrose.

When dialysis is performed, it removes the extraliposomal salt, i.e. ammonium sulfate, but does not remove intra-liposomal ammonium sulfate, thus causing the inside-to-outside chemical gradient across the liposome membrane.

There are many suitable buffer solutions that can be used both to load the drug into the liposomes and to dilute the resulting liposomal composition to a desired concentration of the drug. Since liposomes primarily contain phospholipids, which are stable at around neutral pH of about 6.0 to 8.0, buffer solutions used to load and dilute liposomes should also have a neutral pH. Also, ideally the buffer solution should be suitable for parenteral preparations. Some of the most common buffer solutions used in parenteral preparations, which are suitable in the present invention for loading the drug into the liposomes and for dilution of the liposomal composition, are glycine, phosphate, citrate, acetate, and histidine buffers. Histidine buffer solution is preferable as it has the most stable pH in the neutral range. Preferably, the buffer solution comprises sucrose and histidine hydrochloride in a molar ratio from 29:0.1 to 29:10, more preferably about 29:1. Use of sucrose helps in protecting and rigidifying the liposomal membrane and also in maintaining the isotonicity of the liposomal composition.

After the liposomes are loaded, any untrapped agent is removed. Suitable methods include, but are not limited to, gel filtration chromatography, dialysis, treatment with microporus styrene/divinylbenzene copolymer resin (DOWEX) and subsequent filtration. DOWEX treatment is a preferred method because of its ease of use. When dialysis is used, it is preferably performed in the same manner as described above when removing extraliposomal hydration media salts.

As discussed above, by controlling or reducing the amount of aqueous hydration media, the resulting liposomes have an increased phospholipid content per unit volume. Increase in phospholipid content increases liposome stability, decreases permeability, and thus slows the release of any entrapped agent.

Suitable agents for loading into liposomes of the present invention are water soluble amphipathic compounds with ionizable groups. Amphipathic agents exhibit both hydrophilic and lipophilic characteristics and may be a therapeutic or diagnostic agent. Therapeutic agents may be any desired agent and include antineoplastic agents.

An antineoplastic agent is a drug that prevents, kills, or blocks the growth and spread of cancer cells. There are many suitable antineoplastic agents some of which include Altretamine; Asparaginase; BCG; Bleomycin sulfate; Busulfan; Carboplatin; Carmustine; Chlorambucil; Cisplatin-cis-platimum, cis-diammine-dichloroplatinum; Cladribine, 2-chlorodeoxyadenosine; Cyclophosphamide; Cytarabine-cytosine arabinoside; Dacarbazine imidazole carboxamide; Dactinomycin; Daunorubicin-daunomycin, Daunorubicin hydrochloride; Dexamethasone; Doxorubicin, Doxorubicin hydrochloride; Epirubicin; Etoposide-epipodophyllotoxin; Floxuridine; Fluorouracil; Fluoxymesterone; Flutamide; Fludarabine; Goserelin; Hydroxyurea; Idarubicin HCL; Ifosfamide-Isophosphamide; Interferon alfa; Interferon alfa 2a; Interferon alfa 2b; Interferon alfa n3; Irinotecan; Leucovorin calcium; Leuprolide; Levamisole; Lomustine; megestrol; Melphalan-L-phenylalanine mustard, L-sarcolysin; Melphalan hydrochloride; Mechlorethamine, nitrogen mustard; Methylprednisolone, Methotrexate-Amethopterin, Mitomycin-Mitomycin-C; Mitoxantrone; Mercaptopurine, Paclitaxel; Plicamycin-Mithramycin; Prednisone; Procarbazine; Streptozocin-Streptozotocin; Tamoxifen; 6-thioguanine; Thiotepa-triethylene thiophosphoramide; Vinblastine; Vincristine; or vinorelbine tartrate. Preferred antineoplastic agent of this invention include Doxorubicin hydrochloride, Daunorubicin hydrochloride, and Epirubicin hydrochloride.

The present invention also provides for loading the liposomes with diagnostic agents including, but not limited to, MRI (magnetic resonance imaging) contrast agents (also called paramagnetic agents) used to help provide a clear picture during MRI. MRI is a special kind of diagnostic procedure that uses magnets and computers to create images or "pictures" of certain areas inside the body. Unlike x-rays, it does not involve ionizing radiation. Exemplary MRI diagnostic agents include Gadodiamide; Gadopentetate; Gadoteridol; Gadoversetamide, Gd:diethylenetriaminepentacedic acid chelate (Gd-DTPA) (U.S. Pat. No. 6,132,763).

Once liposomes are loaded, and the unencapsulated, therapeutic/diagnostic agent is removed, the liposomal composition may be aseptically filtered for sterilization making it suitable for parenteral administration. Ideally the filter is at least a 0.2 µm filter. The liposomal composition is then filtered into a sterile depyrogenated bulk container. Subsequently the sterile composition is filled aseptically into sterile depyrogenated smaller containers such as glass vials. The air in the headspace of the container is removed by purging with an inert gas, such as nitrogen and the containers are sealed. By "suitable for parenteral administration" it is meant that the composition is sterile, isotonic and controlled for bacterial endotoxins.

The present invention also provides for stable, long-circulating, low toxicity non-pegylated liposomes. The liposomes are preferably manufactured by the methods described herein. The liposomes of this invention are long circulating non-pegylated liposomes that have a blood circulation half-life of at least 25 times longer than conventional non-liposomal formulations (ADRIAMYCIN), when tested in Swiss albino mice at equivalent doses. A preferred blood circulation half-life is about 40 times longer than that obtained with ADRIAMYCIN.

Non-pegylated liposomes of the present invention are comprised of a phospholipid and cholesterol. Acceptable ratios of phospholipid to cholesterol are described above and are preferably at a molar ratio of about 1:0.1 to 1:2. A preferred molar ratio of phospholipid to sterol is about 1:0.7. Phosphatidyl cholines are preferred phospholipids and disteraroyl phosphatidylcholine (DSPC) is especially preferred.

The non-pegylated liposomes may be loaded with a diagnostic or therapeutic agent. Such agents are known and discussed above. Non-pegylated liposomes of the present invention are preferably loaded using a chemical gradient as discussed above.

A preferred non-pegylated liposome of the present invention is loaded with doxorubicin hydrochloride and is prepared using methods described above. In one embodiment, when loading doxorubicin hydrochloride using the active loading procedure described above, the drug is dissolved in a suitable buffer solution (as described above) before loading to get a concentration of at least 25 mM. When the active loading process involves an ammonium sulfate gradient, the ammonium sulfate reacts with doxorubicin hydrochloride to form doxorubicin sulfate. Doxorubicin sulfate is insoluble and remains inside the liposomes after loading. Once any unentrapped or free drug is removed from loaded liposomes, the drug loaded liposomes are diluted using aqueous buffer solution to achieve the required drug concentration. The preferred buffer solution used is sucrose-histidine buffer solution as discussed previously.

An exemplary non-pegylated liposomal doxorubicin composition contains 2 mg/ml doxorubicin hydrochloride.

Another exemplary non-pegylated liposomal doxorubicin composition contains 4 mg/ml doxorubicin hydrochloride. Using methods of the present invention, the doxorubicin may be loaded into non-pegylated liposomes at a concentration twice of that desired in the final desired composition. Then the loaded liposomes may be diluted with a suitable buffer solution (as described above) to achieve the desired concentration of doxorubicin per ml of liposomal composition. On dilution, the external media in which the liposomes are suspended is diluted, whereas the drug inside the liposomes remains undiluted.

In a preferred embodiment, the molar ratio of doxorubicin hydrochloride to phospholipids is from about 1:2 to about 1:15. A preferred molar ratio is about 1:3.5.

The present invention also provides non-pegylated liposomal doxorubicin compositions. The composition comprises non-pegylated liposomes as described above in suitable pharmaceutically acceptable carriers, which are known in the art. The liposomes have been loaded with doxorubicin hydrochloride. The compositions are suitable for parenteral administration, and are long circulating.

One embodiment provides a long circulating non-pegylated liposomal doxorubicin compositions for parenteral administration. The liposomal composition comprises non-pegylated doxorubicin liposomes in a pharmaceutically acceptable carrier. Suitable pharmaceutically acceptable carriers are known in the art. In a preferred pharmaceutical composition, the concentration of Doxorubicin hydrochloride varies from 1 mM to 10 mM, more preferably about 6.9 mM, and the most preferable is about 3.45 mM. The Molar concentration of phospholipids varies from 10 mM to 15 mM of the parenteral composition. A more preferred content is about 12.15 mM.

The composition further comprises distearoylphosphatidyl choline, cholesterol, histidine hydrochloride, and sucrose. Preferably the liposomes have an average size from 0.06 μm-0.16 μm.

Preferably the doxorubicin hydrochloride content is 1-10 mM and more preferably the doxorubicin hydrochloride content is 3.45 mM.

In the compositions of the present invention, the molar ratio of distearoylphosphatidyl choline to cholesterol is from 1:0.6-1:0.8, and is preferably 1:0.7.

In the compositions of the present invention, the molar ratio of doxorubicin hydrochloride to distearoylphosphatidyl choline is from 1:2-1:10, preferably from 1:2-1:8 and more preferably 1:3.5.

The sucrose content is from 0.1M-0.5M, and more preferably is 0.25M to 0.3M.

In the compositions of the present invention the content of histidine hydrochloride is from 1 mM to 100 mM, preferably 8-12 mM, and more preferably 10 mM.

In the compositions of the present invention, the liposomes have an average size of 0.08 μm-0.12 μm.

In one embodiment of the present invention, the doxorubicin hydrochloride is present at 4 mg/ml, and the molar ratio of doxorubicin to DSPC is 1:3.5, and the ratio of DSPC to cholesterol is 1:0.7.

In yet another embodiment of the present invention, the doxorubicin hydrochloride is present at 2 mg/ml, and the molar ratio of doxorubicin to DSPC is 1:3.5, and the ratio of DSPC to cholesterol is 1:0.7.

The doxorubicin liposomes in the compositions preferably have a half circulation time (t½) in blood at least 40 times longer than ADRIAMYCIN when tested in Swiss albino mice at equivalent doses.

Another embodiment of the present invention provides a method for reducing tumor growth by administering non-pegylated liposomal doxorubicin composition. This method involves administering a therapeutically effective amount of a non-pegylated liposomal doxorubicin composition of the present invention. As non-pegylated liposomal doxorubicin composition have a prolonged circulation time, exhibit decreased toxicity and do not present "Hand-Foot Syndrome" issues, they provide a viable treatment for reducing tumor growth. A skilled practitioner would be able to use the data presented herein as well as common knowledge of dosage amounts, dosage times, and routes of administration, to treat an individual having a tumor susceptible to treatment by doxorubicin hydrochloride with the non-pegylated doxorubicin liposomes of the present invention. The compositions of the present invention having 2 mg/ml and 4 mg/ml doxorubicin hydrochloride strengths are useful for treatment of reducing tumor growth.

The present invention also provides for a process for making these compositions with the ingredients in the same proportions as in the compositions. The process comprises: a process for manufacture of a long circulating non-pegylated liposomal doxorubicin composition for parenteral administration comprising (a) dissolving lipids comprising Distearoylphosphatidylcholine (DSPC) and cholesterol in a single solvent or in a mixture of solvents, (b) removing said solvents before or after hydrating the lipids by addition of an aqueous hydration media to form liposomes in a liposomal composition, wherein said aqueous hydration media comprises ammonium sulfate and sucrose, and wherein the aqueous hydration media is added in quantities in the range of 10 ml to 35 ml per each mmole of DSPC;

(c) sizing the liposomes in the liposomal composition obtained at the end of step (b), to about 0.060 μm-0.16 μm;

(d) removing extraliposomal ammonium sulfate from the liposomal composition that has undergone sizing at step (c), using a sucrose-histidine buffer solution comprising histidine hydrochloride and sucrose;

(e) dissolving doxorubicin hydrochloride in said sucrose-histidine buffer solution to obtain a solution of at least 25 mM doxorubicin hydrochloride concentration;

(f) admixing doxorubicin hydrochloride solution obtained at step (e) and the liposomal composition obtained at the end of step (d) to obtain doxorubicin hydrochloride loaded liposomal composition;

(g) removing extraliposomal doxorubicin hydrochloride from the liposomal composition by a process selected from the group consisting of tangential flow filtration, column chromatography and treatment with resins;

(h) making up the volume of the liposomal composition obtained at the end of step (g) with said sucrose-histidine buffer solution to obtain a liposomal composition of a desired concentration of doxorubicin hydrochloride;

(i) filtering aseptically, the liposomal composition through a sterile 0.2μ sterilising grade filter into a sterile container to obtain said liposomal doxorubicin composition.

The concentration of ammonium sulfate in the aqueous hydration media is not less than 125 mM.

Non-pegylated liposomes containing doxorubicin hydrochloride of the present invention have shown decreased toxic effects as compared to conventional doxorubicin hydrochloride formulations (ADRIAMYCIN) and pegylated liposomal doxorubicin hydrochloride formulations (CAELYX). Table 1, below, provides the results of acute toxicity and pharmacokinetic studies in mice. Non-pegylated doxorubicin liposomes of the present invention as manufactured by the parameters set forth in Example II were compared to commercially available pegylated liposomal doxorubicin formulation, CAELYX and ADRIAMYCIN. The $LD_{50}$ for the non-pegylated doxorubicin liposomes of the present invention is higher than ADRIAMYCIN and CAELYX, thus demonstrating that the non-pegylated doxorubicin liposomes of the present invention have lower toxicity.

TABLE 1

ACUTE TOXICITY AND PHARMACOKINETIC STUDIES IN MICE

| Parameters | Example II | CAELYX | ADRIAMYCIN |
|---|---|---|---|
| $LD_{50}$ (mg/kg) | 16.13 | 13.5 | 10.29 |
| MTD (mg/kg) | 8 | 8 | 5 |
| $C_{max}$ (µg/ml) | 267.54 | 285.74 | 26.8 |
| $T_{max}$ (hours) | 0.085 | 0.085 | 0.085 |
| Kel | 0.0997 | 0.07109 | 4.851811 |
| $T_{1/2}$ (hours) | 6.948 | 9.748 | 0.143 |
| AUC (µg-h/ml) | 1694.024 | 2083.215 | 1.244 |
| Vd (ml) | 1.480 | 1.688 | 41.42 |
| Vd (ml/kg) | 59.20 | 67.52 | 1656.79 |
| Cl (ml/h) | 0.15 | 0.12 | 200.96 |

Abbreviations:
MTD = maximum tolerated dose;
$C_{max}$ = maximum concentration of drug achieved in the plasma;
$T_{max}$ = time taken to achieve the maximum concentration of drug in the plasma;
Kel = elimination constant;
$T_{1/2}$ = time required for the drug concentration in the plasma to get decreased by 50%;
AUC = area under "concentration" vs. "time" curve;
Vd = volume of distribution;
Cl = clearance rate of drug Non-pegylated doxorubicin liposomes of the present invention were used on MCF-7 human breast tumor implanted in mice. The results are provided in Table 2, below. The difference in tumor weight and effectiveness is measured by T/C % (test to control percentage). In this study (Example VI), the highest ratio of T/C using CAELYX is −78 at 12 mg/kg and −34.7 at 6 mg/kg, whereas using the non-pegylated doxorubicin liposomes of the present invention, the highest is −93.4 at 12 mg/kg and −89.43 at 6 mg/kg. These results demonstrate that the non-pegylated doxorubicin liposomal compositions of the present invention appear to be more effective in reducing tumor weight than the currently marketed pegylated liposomal formulation, CAELYX.

TABLE 2

EFFECT ON MCF-7 HUMAN BREAST TUMOR IMPLANTED IN NUDE MICE

| | | Average Tumor Weight (mg) | | | |
|---|---|---|---|---|---|
| Group Day | Saline Control | Composition of Example II (6 mg/kg) | Composition of Example II (12 mg/kg) | CAELYX (6 mg/kg) | CAELYX (12 mg/kg) |
| 1 | 36.5 | 31.5 | 68.4 | 38.3 | 57.88 |
| 5 | 36.75 | 45.33 | 81.6 | 44.3 | 50.75 |
| 9 | 63.13 | 40.17 | 43.6 | 41.5 | 31.38 |
| 12 | 52.38 | 42.83 | 46.1 | 60.17 | 32 |
| 16 | 78.13 | 5.33 | 16.2 | 25 | 27.8 |
| 19 | 94 | 3.33 | 8 | 25 | 22.8 |
| 23 | 95.38 | 3.33 | 4.5 | 16 | 16.6 |
| 26 | 94.38 | 3.33 | 4.5 | 25 | 12.6 |
| Wt. | 43.4 | −28.17 | −63.9 | −13.3 | −45.2 |
| T/C % | NA | −89.43 | −93.4 | −34.7 | −78 |

Anti-tumor activity of non-pegylated doxorubicin liposomes of the present invention against L1210 mouse leukemia cells was tested. The results are provided in Table 3, below. The results of this test (Example VI) show that non-pegylated doxorubicin liposomal compositions of the present invention are as effective as the pegylated liposomes (CAELYX).

TABLE 3

ANTI-TUMOR ACTIVITY AGAINST L1210 MOUSE LEUKEMIA MODEL

| Group | Dosage (mg/kg) | Mice | Survival Time (Days) | Mean Survival Time (Days) | T/C % |
|---|---|---|---|---|---|
| Saline Control | NA | 1/5 | 17 | 16 | NA |
| | | 2/5 | 16 | | |
| | | 3/5 | 17 | | |
| | | 4/5 | 16 | | |
| | | 5/5 | 16 | | |
| Example II | 6 | 1/5 | 20 | 20.4 | 128 |
| | | 2/5 | 20 | | |
| | | 3/5 | 22 | | |
| | | 4/5 | 20 | | |
| | | 5/5 | 20 | | |
| Example II | 12 | 1/5 | 23 | 21.2 | 132 |
| | | 2/5 | 20 | | |
| | | 3/5 | 20 | | |
| | | 4/5 | 20 | | |
| | | 5/5 | 23 | | |
| Caelzx ® | 6 | 1/5 | 18 | 20.4 | 128 |
| | | 2/5 | 22 | | |
| | | 3/5 | 20 | | |
| | | 4/5 | 20 | | |
| | | 5/5 | 22 | | |
| CAELYX | 12 | 1/5 | 18 | 20.6 | 129 |
| | | 2/5 | 22 | | |
| | | 3/5 | 20 | | |
| | | 4/5 | 23 | | |
| | | 5/5 | 20 | | |

T/C %: Test to control percentage

The above results in Tables 1-3 demonstrate that the non-pegylated liposomal doxorubicin composition of the present invention has a lower toxicity profile and a longer circulation time and has proven efficacy of anti-tumor activity in-vivo against MCF-7 and L1210 tumor models.

In order that those skilled in the art can more fully understand this invention, the following examples, which describe the preparation, characterization, and in vivo chemotherapeutic application in an animal model of liposome formulations of this invention, are set forth. These examples are presented solely for purposes of illustration and are not intended to limit the present invention in any way.

EXAMPLES

Doxorubicin hydrochloride used in these Examples was of parenteral grade complying with US Pharmacopoeial specifications. Phospholipids used in these Examples were of parenteral grade. Cholesterol used in these Examples was complying with US Pharmacopoeial specifications. Water used in these Examples was of parenteral grade complying with Water for Injection specifications. All other additives used in these Examples were of parenteral grade. The entire processing was carried out in an area with a controlled environment.

CAELYX (Pegylated liposomal Doxorubicin formulation) manufactured by Ben Venue Laboratories, USA and ADRIAMYCIN (Conventional non-liposomal Doxorubicin formulation) manufactured by Pharmacia & Upjohn, USA were used in animal studies for comparative evaluation with Non-pegylated liposomal Doxorubicin formulations of the present invention. ADRIAMYCIN, which is also referred to herein as "Conventional non-liposomal doxorubicin composition" is a freeze dried sterile powder for injection, each vial containing Doxorubicin hydrochloride 10 mg, Lactose 50 mg, Methylhydroxybenzoate 1 mg. Before use, the freeze dried powder is reconstituted with 5 ml of Water for Injection provided with the pack.

For hematological testing, Cell Counter (Sysmex Automated Hematology Analyzer-KX-21 was used.

Example I

Process of Making A Liposomal Composition Containing Doxorubicin Hydrochloride

Lipid film formation: DSPC (1.565 g) and cholesterol (0.521 g) were dissolved one after the other in chloroform (40 ml) in a rotary evaporator flask. They were mixed until a clear solution was formed. The flask was connected to a Rotary evaporator and the water bath temperature was adjusted to 60° C. The solvent was evaporated under vacuum to form thin film of lipids on the wall of the flask. After releasing the vacuum, the flask was rotated for approximately 5 minutes while passing nitrogen into the flask to dry off any residual solvent.

Hydration: The lipid film in the flask was then hydrated with 60 ml of aqueous hydration media containing ammonium sulfate. The hydration media consists of 10.0 gm of Sucrose, 2.04 gm of Ammonium sulfate, and 100 ml of water. The flask containing the lipid film and hydration media was rotated for 30 minutes on a water bath maintained at 65-68° C. to form liposomes.

Size reduction of liposomes by extrusion: The liposomal suspension obtained from above was sized by extruding successively through filters having pore size from 0.4 μm and to 0.05 μm.

Development of ammonium sulfate gradient: The suspension of the sized liposomes was dialyzed against a sucrose-histidine buffer solution to remove extra-liposomal ammonium sulfate thereby creating a chemical gradient. A tangential flow filtration system fitted with a 300 KD cassette was used for the dialysis. The absence of ammonium sulfate was tested using Nesseler agent.

The sucrose-histidine buffer solution used in the dialysis and drug loading (below) is as follows: 170.0 gm of sucrose, 3.40 gm of histidine HCl, 1.7 Liters of water, and sodium hydroxide at a quantity sufficient to adjust pH to 6.0 to 6.5.

Drug loading: In a round bottom flask, a 15 mg/ml solution of Doxorubicin HCl in sucrose-histidine buffer solution (described above) was prepared to load the liposomal preparation and to get drug loaded liposomes having a concentration of 4 mg/ml of doxorubicin hydrochloride. The sized and dialyzed liposomes from above were added slowly to the round bottom flask and mixed for one hour at 65° C. The drug loaded liposomes were mixed with DOWEX for 30 minutes to remove the unentrapped drug. The drug loaded liposomes were diluted to a 2 mg/ml concentration using sucrose-histidine buffer solution and then aseptically filtered using a sterile 0.22 μm membrane filter. The filtered liposomal doxorubicin composition was then filled aseptically into sterile depyrogenated glass vials and sealed under cover of nitrogen using TEFLON coated rubber bungs.

Example II $LD_{50}$ Comparison of Pegylated Liposomal Doxorubicin Formulations, Non-Liposomal Doxorubicin Composition, And Non-Pegylated Liposomal Doxorubicin Composition of the Present Invention The following liposomal doxorubicin composition was prepared. Each ml of the composition having:

| | |
|---|---|
| DSPC | 9.55 mg |
| Cholesterol | 3.15 mg |
| Doxorubicin Hydrochloride | 2.01 mg |
| Sucrose | 95 mg |
| Histidine Hydrochloride | 2 mg |

The composition was prepared by the same procedure as in Example I. Doxorubicin hydrochloride (216 mg) was dissolved in 14 ml of sucrose-histidine buffer solution and added to 40 ml of sized liposomes and mixed for 1 hour. The resultant drug loaded liposomal dispersion was then passed through a DOWEX column to remove unentrapped drug.

The product obtained after passing through the DOWEX column had the following characteristics:
Product Analysis

| | |
|---|---|
| Total Doxorubicin HCl content | 3.98 mg/ml |
| Entrapped Doxorubicin HCl content | 3.94 mg/ml |

The above product after dilution with histidine buffer to a concentration of 2 mg/ml was analyzed for the following parameters:

| | |
|---|---|
| Appearance | Red colored translucent liquid |
| pH | 6.1 |
| Particle size | Average particle size 0.093 μm |
| DSPC content | 9.55 mg/ml |
| Cholesterol content | 3.15 mg/ml |
| Doxorubicin HCl content | 2.01 mg/ml |
| Bacterial endotoxins | Less than 2.2 EU/mg of doxorubicin hydrochloride. |
| Sterility | Sterile |
| Sucrose content | 9.35% |
| Histidine HCL content | positive |

This composition was subjected to acute toxicity studies in mice. A $LD_{50}$ comparison of "pegylated liposomal doxorubicin composition" (CAELYX), "conventional non-liposomal doxorubicin composition" (ADRIAMYCIN), and "non-pegylated liposomal doxorubicin composition of the present invention" was performed.

| | |
|---|---|
| Animals used | Swiss albino mice of either sex. |
| Weight range of animal | 20–22 gm. |
| Number of groups | 3 |
| Number of animals per group | 10 |

Animals were divided into 3 groups and each group comprised of ten animals. GROUP 1 received Composition of Example II, GROUP 2 received CAELYX, and GROUP 3 received ADRIAMYCIN.

All animals received injections via the intravenous route. The drug solutions were suitably diluted with dextrose (5% w/v) solution before administering to the animals. The animals were then observed for a period of 14 days. They were observed for any clinical toxicity and mortality.

The $LD_{50}$ values of the different Doxorubicin compositions studied are provided in Table 1. The $LD_{50}$ dose was found to be 16.13 mg/kg whereas the $LD_{50}$ dose for the marketed conventional preparation (ADRIAMYCIN) was 10.29 mg/kg. The $LD_{50}$ for the marketed pegylated liposomal preparation CAELYX was 13.5 mg/kg. These results show that non-pegylated liposomes of the present invention have a reduced toxicity as compared to other Doxorubicin formulations and to pegylated-liposomal Doxorubicin formulations.

Example III

Comparison of Subacute Toxicity of "Non-Pegylated Liposomal Doxorubicin Composition of the Present Invention With "Pegylated Liposomal Doxorubicin Composition" (CAELYX) And "Conventional Non-Liposomal Doxorubicin Composition" (ADRIAMYCIN)."

| | |
|---|---|
| Animals used | Swiss albino mice of either sex |
| Number of groups | 11 |
| Number of animals per group | 8 |
| Weight range of animal | 19–23 gms |
| Route of administration | Intravenous |

Animals were divided into 11 groups, each group comprising of eight animals. GROUP 1 received Dextrose 5% Injection, GROUP 2 received blank liposomes (before drug loading) of the present invention, GROUP 3, GROUP 4 and GROUP 5 received Composition of Example II at different doses, GROUP 6, GROUP 7 and GROUP 8 received CAELYX at different doses, GROUP 9, GROUP 10 and GROUP 11 received ADRIAMYCIN at different doses. The doses are provided in Table 4.

TABLE 4

DOSES OF DOXORUBICIN FORMULATIONS FOR REPEAT DOSE TOXICITY STUDIES IN MICE

| Group No. | Group | Dose (mg/kg body weight) | Cumulative dose (mg/kg body weight) |
|---|---|---|---|
| 1 | Dextrose | — | — |
| 2 | Blank liposomes | — | — |
| 3 | Composition of | 1 | 7 |
| 4 | Example II | 2 | 14 |
| 5 | | 3 | 21 |
| 6 | CAELYX | 1 | 7 |
| 7 | | 2 | 14 |
| 8 | | 3 | 21 |
| 9 | ADRIAMYCIN | 1 | 7 |
| 10 | | 2 | 14 |
| 11 | | 3 | 21 |

All groups received injections on alternate days, for fourteen days via the intravenous route. The formulations were suitably diluted with Dextrose 5% Injection before administration to the animals. The animals were observed during the study period of 14 days for the following:
→Mortality
→Clinical signs and symptoms
→Body weights
→Food consumption
→Organ weights Results Mortality: The percent mortality over a period of fourteen days was recorded for all the formulations.

TABLE 5

PERCENT MORTALITY FOR THE VARIOUS DOSES OF DOXORUBICIN COMPOSITIONS

| Group | Dose (Mg/Kg Body Weight) | Percent Mortality |
|---|---|---|
| Dextrose | — | 0 |
| Blank liposomes | — | 0 |
| Composition of Example II | 1 | 0 |
| | 2 | 0 |
| | 3 | 0 |
| CAELYX | 1 | 0 |
| | 2 | 0 |
| | 3 | 0 |
| ADRIAMYCIN | 1 | 0 |
| | 2 | 0 |
| | 3 | 12.5 |

Clinical signs: During the course of study, shedding of tail skin and Alopecia was observed in all Doxorubicin treated groups. Shedding of tail skin was observed in animals after five injections. Dose dependent alopecia was observed in all of the doxorubicin treated animals. Table 6 details the alopecia during the course of this study.

TABLE 6

INCIDENCE OF ALOPECIA IN MICE TREATED WITH VARIOUS DOXORUBICIN COMPOSITIONS

| Formulation | Grading of alopecia |
|---|---|
| Dextrose | — |
| Blank Liposomes | — |
| Composition of Example II (1 mg/kg) | + |
| Composition of Example II (2 mg/kg) | + |
| Composition of Example II (3 mg/kg) | ++ |
| CAELYX (1 mg/kg) | Piloerection # |
| CAELYX (2 mg/kg) | + |
| CAELYX (3 mg/kg) | ++ |
| ADRIAMYCIN (1 mg/kg) | + |
| ADRIAMYCIN (2 mg/kg) | ++ |
| ADRIAMYCIN (3 mg/kg) | ++++ |

Piloerection (raising of hair) was observed in one out of 8 animals on day 12 of the treatment.
+ One out of 8 animals showed alopecia
++ Two out of 8 animals showed alopecia
+++ Three out of 8 animals showed alopecia
++++ Four out of 8 animals showed alopecia Body weight: The body weight of animals were recorded on day 1, day 4, day 7 and day 14. At the dose of 2 mg/kg and 3 mg/kg, a decrease in the body weights was observed in all drug treated groups. The weight loss was significantly different from the control. The body weight of animals receiving blank liposomes was comparable to the dextrose group.

Food Consumption: From a period of 4 to 14 days Doxorubicin treated animals showed in general a decrease in food consumption.

Organ weights: The organs of surviving animals were collected and weighed. The mean organ weights of all the animals were found to be comparable in all drug treated groups.

Example IV

Evaluation of Pharmacokinetic of "Non-Pegylated Liposomal Doxorubicin Composition of the Present Invention" With "Pegylated Liposomal Doxorubicin Composition" (CAELYX) And "Conventional Non-Liposomal Doxorubicin Composition" (ADRIAMYCIN) In Mice

| | |
|---|---|
| Animals used | Swiss albino mice of either sex |
| Number of groups | 3 |
| Number of animals per group | 48 |
| Animal body weight | 25–30 gm |
| Dose for pharmacokinetic study | 10 mg/kg |
| Time points | 5 min, 30 min, 1 hr, 2 hr, 5 hr, 10 hr, 15 hr, 20 hr |
| Number of mice per time point | 6 mice |
| Route of administration | Intravenous |

Blood samples after collection were centrifuged at 4000 rpm for 20 min and the plasma was separated and frozen at −20° C. until analyzed. The frozen plasma was thawed and used for analysis.

1 ml of acetonitrile was added to 100 µL of plasma, vortexed for 10 mins, centrifuged at 3250 rpm for 10 mins. The supernatant was withdrawn and 0.5 ml of saturated $ZnSO_4$ solution was added to it. The resulting solution was vortexed for 5 mins and then centrifuged for 10 mins at 3250 rpm speed. The upper organic layer was then withdrawn and dried under oxygen free nitrogen gas at 60° C. The residue obtained was then reconstituted with 200 µL of Solvent A containing $ZnSO_4$. 100 µL of this solution was then injected in the HPLC column.

| | |
|---|---|
| Instrument | Shimadzu Liquid Chromatograph LC-10AT$_{VP}$ |
| Column | C8 Thermoquest hypersil MOS (250 × 4.6 mm, 5 µ) |
| Column Temp | Ambient |
| Mobile Phase | Solvent A: Acidified Water (pH 2.5, adjusted with 60% Perchloric acid) & Tetrahydrofuran (80:1, v/v) |
| | Solvent B: Acetonitrile |
| | Solvent A: Solvent B (40:60) |
| Flow Rate | 1 ml/min |
| Detector | Fluorescent Detector (RF - 10 AXL Shimadzu; Ex 460 nm and Em 550 nm |
| Run time | 15 mins |

Statistical Analysis

Student's t-test was used for comparison between the three formulations. The results are summarized in Table 1.

Example V

Comparison of Subacute Toxicity of "Non-Pegylated Liposomal Doxorubicin Composition of the Present Invention With "Conventional Non-Liposomal Doxorubicin Composition" (ADRIAMYCIN)" In Dogs

| | |
|---|---|
| Animals used | Dogs |
| Number of groups | 3 |
| Number of animals per group | 3 |
| Weight range of animal | 10–20 kgs |
| Dosage & administration | 1 mg/kg by Intravenous infusion over 20 minutes. Administration was done once a week (i.e. after 7 days) for 4 doses. |

Pharmacological evaluation
→Clinical signs of toxicity
→Body weight
→Haemodynamic parameters
→Haematology
→Biochemical parameters

TABLE 7

CLINICAL SIGNS OF TOXICITY

| Signs | Control (Dextrose Inj. 5%) | ADRIAMYCIN | Composition of Example II |
|---|---|---|---|
| Dermal lesion | None of the signs were seen in this group | Alopecic lesions, erythemic lesions seen after third dose | None of the signs were seen in this group |
| Vomiting | | At first and second dose - ⅔ Third and fourth dose - ⅓ | |
| Diarrhea | | ⅓ at after second, third and fourth dose | |
| Others | | Anorexia | |

Body weight: ADRIAMYCIN treated groups showed decrease in the body weight whereas Control and Composition of Example II treated groups showed no change in body weight.

TABLE 8

HAEMODYNAMIC PARAMETERS

| Parameters | Control (Dextrose Inj. 5%) | ADRIAMYCIN | Composition of Example II |
|---|---|---|---|
| Blood pressure | Normal | Normal | Normal |
| Heart rate | Normal | Increases by average + 29.17% | Normal |
| Respiratory rate | Normal | Decreases by average − 42.12% | Normal |
| Temperature | | Increases body temperature during and after administration (clinically non-significant) | |

Hematological parameters studied:
→RBC
→Total WBC and Differential WBC
→Hemoglobin
→Hematocrit
→Mean Corpuscular volume
→Platelet All the above parameters studied were within normal range in all the groups Biochemical parameters—Increase in Creatinine phosphokinase and lactate dehydrogenase levels were found in ADRIAMYCIN treated groups whereas in control and the composition of Example II, there was no significant change observed.

Liver Function Test (LFT)—Increase in Aspartate aminotranferase, alanine aminotranferase and total bilirubin levels were observed in ADRIAMYCIN treated groups whereas in control and the composition of Example II no significant changes were observed.

Kidney Function Test (KFT)—Increase in Blood Urea Nitrogen (BUN) and creatinine were observed in ADRIA- MYCIN treated groups whereas control showed no increase. Animal group treated with composition of Example II showed an increase in both BUN and creatinine levels, which however, were significantly less than ADRIAMYCIN treated groups.

Example VI

Evaluation of the Anti-Tumor Activity of "Non-Pegylated Liposomal Doxorubicin Composition of the Present Invention" With "Pegylated Liposomal Doxorubicin Composition" (CAELYX) Against L1210 Mouse Leukemia And MCF-7 Human Breast Tumor Implanted In Nude Mice Dose Preparation: Both the above doxorubicin formulations were diluted to 1 mg/ml with sterile normal saline (0.9%). Appropriate volumes of drug solution was administered to various test groups on the basis of body weight so that the animals received the drug as indicated in Tables 9 and 10.

Six week old female NCr nude (nu/nu) mice were used in both models. The animals were housed in polycarbonate micorisolator cages as specified in the Guide for Care and Use of Laboratory Animals (ILAR publication, 1996, National Academy Press). The rooms were well ventilated (greater than 10 air changes per hour) with 50% fresh air. A 12-hour light/12-hour dark photoperiod was maintained. The room temperature was maintained between 18-26° C.

The study animals were acclimatized for at least 3 days prior to tumor inoculation.

General Description: Both liposomal formulations listed above were tested in L1210 mouse leukemia and MCF-7 human breast tumor models at two concentrations each against a control group receiving saline.

L1210 Model

Tumor Cells: L1210 mouse leukemia cell line was obtained from ATCC and propagated using standard in vitro cell expansion methods. The cells were grown in culture media with appropriate supplements and 10% Fetal bovine serum (FBS). The culture was then grown in 35 T-225 flasks to 80-90% confluence. The cells were harvested by centrifugation and the pelleted cells were resuspended in serum-free RPMI to $10^6$ viable cells/ml. The animals were injected with 0.1 ml of cell suspension using a 25 G needle.

Groups and Dosages: Each group consisted of 5 animals. Mice were inoculated intraperitoneally with $10^6$ tumor cells/mouse. Both the liposomal formulations were administered intravenously on day 1, 5 and 9 at dosages shown in Table 9. The animals were observed for 30 days post treatment and mortality was recorded.

TABLE 9

| Group No. | Number of Males/Females | Article | Total Dose (mg/kg) | Dose/injection (mg/kg) | Total number of doses |
|---|---|---|---|---|---|
| 1 | 0/5 | Saline | NA | NA | 3 |
| 2 | 0/5 | CAELYX | 12 | 4 | 3 |
| 3 | 0/5 | CAELYX | 6 | 2 | 3 |
| 4 | 0/5 | Composition of Example II | 12 | 4 | 3 |
| 5 | 0/5 | Composition of Example II | 6 | 2 | 3 |

The animals were examined daily and weighed twice every week and the weights were recorded. Any mortality during the course of the study was recorded.

The anti-tumor activity of both the liposomal formulations were evaluated by comparing the mean survival time in each treated group to that of the controls which received saline. The results were expressed in terms of T/C ratios which was calculated as follows:

$$T/C\ \% = \frac{\text{Mean survival time of test group}}{\text{Mean survival time of control group}} \times 100$$

A T/C≥125% is considered significant activity.

The results of anti-tumor activity against L1210 Mouse leukemia model are provided in Table 3. Mortalities ranged from 15 to 26 days after the first injection (Day 1). The mean survival time of the control group, which received saline was 16.5 days. Increase in the survival time was observed in both the drug treated groups. Both the drug treated groups showed similar difference in the mean survival time (T/C %) indicating that the composition of Example II is as efficacious as CAELYX against L1210 tumor model.

MCF-7 Model

Tumor Cells: MCF-7 human breast tumor cell line was obtained from ATCC and propagated using standard in vitro cell expansion methods. The cells were grown in culture media with appropriate supplements and 10% FBS. The culture was then grown in 35 T-225 flasks to 80-90% confluence. The cells were harvested by centrifugation and the pelleted cells were trypsinized and resuspended in serun-free RPMI to $10^7$ viable cells/ml. The animals were injected with 0.1 ml of cell suspension using a 25 G needle.

Groups and Dosages: Each group consisted of 5 animals. Mice were implanted with estrogen pellets 5 days prior to inoculation. They were inoculated subcutaneously with $10^7$ tumor cells/mouse. The tumor was allowed to grow until they reach a size of 30-100 mm³. Once appropriate size has been reached ($5^{th}$ day after inoculation), mice were be dosed intravenously with the test article on day 1, 5 and 9 as shown in Table 10. Tumor size was measured using a caliper twice weekly up to 30 days post treatment initiation.

TABLE 10

| Group No. | Number of Males/Females | Article | Total Dose (mg/kg) | Dose/injection (mg/kg) | Total number of doses |
|---|---|---|---|---|---|
| 1 | 0/5 | Saline | — | — | — |
| 2 | 0/5 | CAELYX | 12 | 4 | 3 |
| 3 | 0/5 | CAELYX | 6 | 2 | 3 |
| 4 | 0/5 | Composition of Example II | 12 | 4 | 3 |
| 5 | 0/5 | Composition of Example II | 6 | 2 | 3 |

The animals were examined daily and weighed twice every week and the weights were recorded. The length and the width for tumors of individual mice was measured twice a week using calipers and the approximate tumor weight (mg) from tumor dimensions (mm×mm) was calculated using the formula for volume of a prolate ellipsoid:

$$\frac{L \times W^2}{2}$$

where L is the longer of the two measurements.

The anti-tumor activity of both the liposomal formulations were evaluated by comparing the change in tumor weight for treated group to that of the controls, which received saline.

The change in tumor weight was calculated by subtracting the group median tumor weight on day 5 post-inoculation of tumor cells from group median tumor weight on the final evaluation day (day 30 post-treatment).

$$vWt = Wt_{final} - Wt_{initial}$$

The T/C ratio for all test groups was calculated as follows:

$$T/C\% = vWt\ Test/Wt_{initial}\ of\ Test \times 100$$

A T/C 20% is considered necessary to demonstrate moderate activity. A T/C 10% is considered significant activity.

The anti-tumor activity against MCF-7 human breast tumor model is tabulated in Table 2.

TABLE 11

EARLY DEATHS IN VARIOUS GROUPS OF ANIMALS

| Group | Dosage | Mortality |
|---|---|---|
| Control | Nil | 0/5 |
| Composition of Example II | 6 mg/kg | 0/5 |
| Composition of Example II | 12 mg/kg | 0/5 |
| CAELYX | 6 mg/kg | 2/5 |
| CAELYX | 12 mg/kg | 1/5 |

Tumors in the control group continued to grow throughout duration of the study reaching a maximum of 116.4 mg on the 26$^{th}$ day whereas tumors in the treated mice regressed significantly during the course of the study. The tumors disappeared completely in the group receiving 12 mg/kg of composition of Example II formulation indicating that composition of Example II is effective against MCF-7 human breast tumors.

Several early deaths occurred in various groups as shown in Table 11. However, the cause of deaths seemed to be unrelated to the tumors. There were no deaths in the saline control group, which had the largest tumors. Some of the dead animals were necropsied, and all of them were found to have thickened, abnormal bladders. At the termination of the study, many of the euthanized mice, likewise had thickened bladders. Histopathological examination of one of the thickened bladders revealed no evidence of tumor metastasis. Premature death of estrogenised, tumor-implanted nude mice due to the incidence of urogenital disease.

Example VII

Determination of Maximum Tolerated Dose (MTD) And To Assess Therapeutic Efficacy of Doxorubicin Liposomes of the Present Invention In Nude Athymic Mice With A121 Human Ovarian Tumor Maximum tolerated dose and assessment of therapeutic efficacy of Doxorubicin liposomes of the present invention in nude athymic mice with A121 human ovarian tumor was carried out in comparison with Conventional non-liposomal formulation (ADRIAMYCIN) and Pegylated liposomal formulation (CAELYX).

Nude athymic Ncr-nu/nu mice [4 mice/group (10 in Control group)] were implanted subcutaneously with human A121 ovarian tumour via trocar implant. A total of 46 animals were used in this experiment. A total of 46 animals were utilised for the experiment. Equivalent doses of ADRIAMYCIN, CAELYX and the composition of Example II were evaluated intravenously. Drugs were administered intravenously via tail vein of mice on day 5 and 12 after tumour implant.

All treatment groups demonstrated good antitumor efficacy.
The dosage schedule is presented below.
Dosing schedule
Control Mice: The control mice received no treatment.
ADRIAMYCIN
12 mg/kg (6 mg/kg×2 inj)
24 mg/kg (12 mg/kg×2 inj)
36 mg/kg (18 mg/kg×2 inj)
CAELYX
12 mg/kg (6 mg/kg×2 inj)
24 mg/kg (12 mg/kg×2 inj)
36 mg/kg (18 mg/kg×2 inj)
Composition of Example II
12 mg/kg (6 mg/kg×2 inj)
24 mg/kg (12 mg/kg×2 inj)
36 mg/kg (18 mg/kg×2 inj)

All mice receiving the highest dosage 36 mg/kg of free drug (18 mg/kg×2 ADRIAMYCIN) and 3 of 4 mice that received the intermediate dosage of 24 mg/kg died as a result of drug toxicity. The maximum tolerated dose (MTD) of ADRIAMYCIN is hence less than 24 mg/kg.

Mice tolerated both CAELYX and the composition of Example II. Both the formulations were well tolerated at 36 mg/kg. However, CAELYX appeared to cause more toxicity than the composition of Example II and produced a greater weight loss of mice receiving the high dose (36 mg/kg).

This study demonstrates that the composition of Example II is better tolerated than the commercially available pegylated liposomal preparation (CAELYX) and conventional non-liposomal formulation (ADRIAMYCIN).

Example VIII

To Assess the Efficacy of Liposomal Doxorubicin Composition of the Present Invention In Nude Athymic Mice Implanted With A Multidrug Resistant, Pgp Positive, Human Colon DLD1 Tumor Xenografts The composition of Example II along with CAELYX and ADRIAMYCIN were subjected to efficacy studies in nude athymic mice implanted s.c. with the drug resistant (Pgp+) DLD-1 human colon tumor.

Animals, nude athymic mice, 4 mice/group (10 in Control group) implanted subcutaneously with human DLD-1 colon tumor via trocar implant.
Control: No treatment
ADRIAMYCIN
12 mg/kg (6 mg/kg×2 inj)
24 mg/kg (12 mg/kg×2 inj)
CAELYX
24 mg/kg (12 mg/kg×2 inj)
36 mg/kg (18 mg/kg×2 inj)
48 mg/kg (24 mg/kg×2 inj)
Composition of Example II
24 mg/kg (12 mg/kg×2 inj)
36 mg/kg (18 mg/kg×2 inj)
48 mg/kg (24 mg/kg×2 inj)
A total of 42 animals were utilised for the experiment.
Results The dosages of ADRIAMYCIN were lowered to 12 and 24 mg/kg in this study based on the toxicity observed in Example VII following the administration of 36 mg/kg free drug. In contrast, dosages of CAELYX and the composition of Example II were increased to 48 mg/kg to compare their efficacies and toxicities with the free drug at their respective MTDs. All agents were administered to nude athymic mice i.v. via tail vein on day 5 and 12 after s.c. tumor implant with the multidrug resistant, Pgp positive, human colon tumor xenograft. All treatments groups demonstrated antitumor efficacy.

However, mice receiving either of the liposomal preparations demonstrated significantly greater antitumor efficacy. At equivalent free drug dosages (24 mg/kg), a median tumor growth delay of 10 days was observed with the free drug, while all mice administered liposomal preparations had tumors that were less than 600 nm³ on day 40. No toxicity was evident at dosages of 36 mg/kg for either CAELYX or Composition of Example II.

At the highest dosages (48 mg/kg) both liposomal drug formulations (24 mg/kg×2, CAELYX or Composition of Example II), mice demonstrated >15% weight loss, and 1 of 4 animals of each of those groups died early (day 17, 19) as a result of drug toxicity. Therefore, the MTD of the both liposomal formulations was similar and appeared to be less than 48 mg/kg.

In contrast to ADRIAMYCIN, the two liposomal formulations [CAELYX—(pegylated doxorubicin) and Composition of Example II (non-pegylated-doxorubicin)] displayed significant antitumor efficacy against s.c. implanted, Pgp positive, multidrug resistant human DLD1 colon tumors in nude athymic mice. At equivalent dosages of 24 mg/kg, both liposomal formulations displayed increased efficacy as compared with the free drug. In addition, both liposomal formulations displayed lower toxicities as compared with the free drug allowing more drug to be administered. The MTD for ADRIAMYCIN appears to be about half that of the liposomal formulations. Liposomal drug dosages of 36 mg/kg were well tolerated.

Example IX to XIII

The Composition And Process of Example IX To XIII Are Given In Table 12.

TABLE 12

| Ingredients | Example IX | Example X | Example XI | Example XII | Example XIII |
|---|---|---|---|---|---|
| | Parameters changed | | | | |
| | Increased Particle size | Less Cholesterol | Higher cholesterol | C14 phospholipid | Conventional hydration |
| DSPC | 1.565 g | 1.565 g | 1.565 g | — | 1.565 g |
| DMPC | — | — | — | 1.565 g | — |
| Cholesterol | 0.521 g | 0.3 g | 0.74 g | 0.521 g | 0.521 g |
| Chloroform | 40 ml | 40 ml | 40 ml | 40 ml | 40 ml |
| Hydrating medium | 60 ml | 60 ml | 60 ml | 60 ml | 120 ml |
| Average particle Size | 0.18 μm | 0.085 μm | 0.095 μm | 0.095 μm | 0.085 μm |
| Histidine Buffer | 1.7 lt. | 1.7 lt. | 1.7 lt. | 1.7 lt. | 1.7 lt. |
| Doxorubicin HCl | 330 mg | 330 mg | 330 mg | 330 mg | 330 mg |
| Histidine buffer (for solubilizing the drug) | 22 ml | 22 ml | 22 ml | 22 ml | 40 ml |
| Histidine buffer (for dilution) | 80 ml | 80 ml | 80 ml | 80 ml | — |

Procedure:

The Procedure of Example I was followed for Example X, XI and XII.

In Example IX procedure of Example I was followed except for the size reduction of liposomes which was carried out by extruding through membranes of 0.4μ to 0.2μ to get an average size in the range of 0.15 μm to 0.25 μm.

In Example XIII procedure of Example II was followed except for the volume of hydration which was doubled.

The results of toxicological testing are given in Table 13.

TABLE 13

| Results | Example IX | Example X | Example XI | Example XII | Example XIII |
|---|---|---|---|---|---|
| | Observations | | | | |
| | Parameters changed | | | | |
| | Increased Particle size | Less Cholesterol | Higher cholesterol | C14 phospholipid | Conventional hydration |
| $T_{1/2}$ in mice | 2 hrs ($C_{max}$ and | 3 hrs | 5 hrs ($C_{max}$ and | 2 hrs | 4 hrs |

TABLE 13-continued

| | Observations | | | | |
|---|---|---|---|---|---|
| | Example IX | Example X | Example XI | Example XII | Example XIII |
| | Parameters changed | | | | |
| Results | Increased Particle size | Less Cholesterol | Higher cholesterol | C14 phospholipid | Conventional hydration |
| $LD_{50}$ in mice Conclusion (with reference to composition of Example I) | AUC not comparable) 12 mg/kg $T_{1/2}$ significantly less | 10 mg/kg $T_{1/2}$ significantly less and increased toxicity | AUC not comparable) 12 mg/kg $C_{max}$ and AUC were significantly less | 10 mg/kg $T_{1/2}$, $C_{max}$, AUC significantly less | 14 mg/kg Less $T_{1/2}$ |

Example XIV

Liposomal Doxorubicin Composition Without Sucrose

Lipid film formation: Distearoylphosphatidylcholine (1.565 g) and cholesterol (0.521 g) were dissolved one after the other in chloroform (40 ml) in a rotary evaporator flask. They were mixed until a clear solution was formed. The flask was connected to a Rotary evaporator and the water bath temperature was adjusted to 60° C. The solvent was evaporated under vacuum to form thin film of lipids on the wall of the flask. After releasing the vacuum, the flask was rotated for approximately 5 minutes while passing nitrogen into the flask to drive off any residual solvent.

Hydration: The lipid film was hydrated with 60 ml of aqueous hydration media. The aqueous hydration media was 2.04% w/v Ammonium sulfate in water. The flask containing the lipid film and hydration media was rotated for 30 minutes on a water bath maintained at 65-68° C. to form blank liposomes.

Size reduction of blank liposomes by extrusion: The liposomal suspension obtained from above was sized by extruding successively through filters having pore size from 0.4 μm and to 0.05 μm.

Dialysis: The suspension of the sized liposomes was dialyzed against a 0.2% w/v histidine hydrochloride solution of pH 6.5. A tangential flow filtration system was used for the dialysis. The dialysis was continued till extra liposomal ammonium sulfate was removed. The absence of ammonium sulfate in extra liposomal media was confirmed using Nesseler reagent.

Drug loading: In a round bottom flask, a 15 mg/ml solution of Doxorubicin HCl was prepared by dissolving 216 mg of Doxorubicin hydrochloride in 14 ml of histidine hydrochloride solution (described above). The measured volume (40 ml) of sized and dialyzed liposomes from above were added slowly to the round bottom flask and mixed for one hour at 65° C.

The drug loaded liposomes were treated with DOWEX to remove the unentrapped drug.

The samples of the composition obtained before and after treatment with DOWEX were analysed for Doxorubicin hydrochloride content by high pressure liquid chromatography (HPLC). The results are as follows:

| Total Doxorubicin HCl content (before DOWEX treatment) | 4.02 mg/ml |
|---|---|
| Entrapped Doxorubicin HCl content (after DOWEX treatment) | 4 mg/ml |

The doxorubicin hydrochloride loaded liposomes after removing the free drug were diluted to a 2 mg/ml of doxorubicin hydrochloride concentration using solution of histidine hydrochloride and sucrose (described above). The liposomal composition thus obtained was then aseptically filtered using a sterile 0.22 μm membrane filter into a sterile depyrogenated container and was analyzed for the following parameters:

| Appearance | Red colored translucent liquid |
|---|---|
| pH | 6.3 |
| Particle size | Average particle size 0.097 μm |
| Doxorubicin HCl content | 2.05 mg/ml |
| Bacterial endotoxins | Less than 2.2 EU/mg of doxorubicin hydrochloride. |
| Sterility | Sterile |

Stability studies on the compositions obtained in this example were carried out and the observations are given in Table 14.

Example XV

Process of Making A Liposomal Doxorubicin Composition With 120 mM Ammonium Sulfate Solution Lipid film formation: Distearoylphosphatidylcholine (1.565 g) and cholesterol (0.521 g) were dissolved one after the other in chloroform (40 ml) in a rotary evaporator flask. They were mixed until a clear solution was formed. The flask was connected to a Rotary evaporator and the water bath temperature was adjusted to 60° C. The solvent was evaporated under reduced pressure to form thin film of lipids on the wall of the flask. After releasing the vacuum, the flask was rotated for approximately 5 minutes while passing nitrogen into the flask to drive off any residual solvent.

Hydration: The lipid film was hydrated with 60 ml of aqueous hydration media. The aqueous hydration media consists of Sucrose 10% w/v, Ammonium sulfate 1.58% w/v in water. The flask containing the lipid film and hydration media was rotated for 30 minutes on a water bath maintained at 65° C.-68° C. to form blank liposomes.

Size reduction of blank liposomes by extrusion: The liposomal suspension obtained from above was sized by extruding successively through filters having pore size from 0.4 µm and to 0.05 µm.

Dialysis: The suspension of the sized liposomes was dialyzed against a histidine buffer. A tangential flow filtration system was used for the dialysis. The dialysis was continued till extra liposomal ammonium sulfate was removed. The absence of ammonium sulfate in extra liposomal media was confirmed using Nesseler reagent. The histidine hydrochloride solution used in the dialysis and drug loading (below) was as follows: 170.0 gm of sucrose, 3.40 gm of histidine HCl, 1.7 Liters of water, and sodium hydroxide at a quantity sufficient to adjust pH to 6.0 to 6.5.

Drug loading: In a round bottom flask, a 15 mg/ml solution of Doxorubicin HCl was prepared by dissolving 216 mg of Doxorubicin hydrochloride in 14 ml of histidine hydrochloride solution (described above). The measured volume (40 ml) of sized and dialyzed liposomes from above were added slowly to the round bottom flask and mixed for one hour at 65° C.

The drug loaded liposomes were treated with DOWEX to remove the unentrapped drug.

The samples of the composition obtained before and after treatment with DOWEX were analysed for Doxorubicin hydrochloride content by high pressure liquid chromatography (HPLC). The results are as follows:

| | |
|---|---|
| Total Doxorubicin HCl content (before DOWEX treatment) | 4.11 mg/ml |
| Entrapped Doxorubicin HCl content (after DOWEX treatment) | 4.10 mg/ml |

The doxorubicin hydrochloride loaded liposomes after removing the free drug were diluted to a 2 mg/ml of doxorubicin hydrochloride concentration using solution of histidine hydrochloride and sucrose (described above). The liposomal composition thus obtained was then aseptically filtered using a sterile 0.22 µm membrane filter into a sterile depyrogenated container and was analyzed for the following parameters:

| | |
|---|---|
| Appearance | Red colored translucent liquid |
| pH | 6.35 |
| Particle size | Average particle size 0.09 µm |
| Doxorubicin HCl content | 2.03 mg/ml |
| Bacterial endotoxins | Less than 2.2 EU/mg of doxorubicin hydrochloride. |
| Sterility | Sterile |

Stability studies on the composition obtained in this example were carried out an the observations are given in Table 14.

Example XVI

Composition of Example XIV, Example XV Along With the Composition of Present Invention (Example II) Were Subjected For Short-Term Stability Studies At Accelerated Temperature (25° C.)

Results of doxorubicin content are given in Table 14.

TABLE 14

| | Composition of | | | | Example XV | |
|---|---|---|---|---|---|---|
| | Example II | | Example XIV | | | Total |
| | Entrapped (mg/ml) | Total (mg/ml) | Entrapped (mg/ml) | Total (mg/ml) | Entrapped (mg/ml) | (mg/ml) |
| Initial | 2.01 | 2.01 | 2.05 | 2.05 | 2.03 | 2.03 |
| 25° C.-1 week | 2.01 | 2.01 | 1.86 | 2.04 | 1.84 | 2.03 |

This example shows that the presence of sucrose is essential for reducing leakage of encapsulated doxorubicin and ammonium sulfate concentration in the hydration media is important. A concentration of 120 mM leads to the leakage of encapsulated doxorubicin and hence is not satisfactory. However, the composition of Example II containing sucrose and ammonium sulfate in a concentration of 155 mM did not leak the encapsulated doxorubicin during the study duration.

Example XVII

Preparation of Liposomal Doxorubicin Composition By the Process of Solvent Removal After Hydration Distearoylphosphatidylcholine (1.565 g) and cholesterol (0.521 g) were dissolved one after the other in ethanol (20 ml) and pumped slowly under pressure into the aqueous hydration media which was constantly stirred. The aqueous hydration media consisted of Sucrose 10% w/v, Ammonium sulfate 2.04% w/v in water. This lipid solution containing the solvent ethanol was transferred to rotary evaporator flask. Flask was connected to a Rotary evaporator and the water bath temperature was adjusted to 60° C. Ethanol was removed under vacuum.

Size reduction of blank liposomes by extrusion: The liposomal suspension obtained from above was sized by extruding successively through filters having pore size from 0.4 µm and to 0.05 µm.

Dialysis: The suspension of the sized liposomes was dialyzed against a histidine buffer. A tangential flow filtration system was used for the dialysis. The dialysis was continued till extra liposomal ammonium sulfate was removed. The absence of ammonium sulfate in extra liposomal media was confirmed using Nesseler reagent. The histidine hydrochloride solution used in the dialysis and drug loading (below) was as follows: 170.0 gm of sucrose, 3.40 gm of histidine HCl, 1.7 Liters of water, and sodium hydroxide at a quantity sufficient to adjust pH to 6.0 to 6.5.

Drug loading: In a round bottom flask, a 15 mg/ml solution of Doxorubicin HCl was prepared by dissolving 216 mg of Doxorubicin hydrochloride in 14 ml of histidine hydrochloride solution (described above). The measured volume (40 ml) of sized and dialyzed liposomes from above were added slowly to the round bottom flask and mixed for one hour at 65° C.

The drug loaded liposomes were treated with DOWEX to remove the unentrapped drug.

The doxorubicin hydrochloride loaded liposomes after removing the free drug were diluted to a 2 mg/ml of doxorubicin hydrochloride concentration using solution of histidine hydrochloride and sucrose (described above). The liposomal composition thus obtained was then aseptically filtered using a sterile 0.22 μm membrane filter into a sterile depyrogenated container.

A summary of the toxicological and efficacy studies carried out are as follows:

Example II—Non-pegylated long circulating liposomes containing doxorubicin hydrochloride of the present invention have shown decreased toxic effects as compared to non-liposomal doxorubicin hydrochloride formulations (ADRIAMYCIN) and pegylated liposomal doxorubicin hydrochloride formulations (CAELYX). The $LD_{50}$ for the non-pegylated doxorubicin liposomes of the present invention is higher than the CAELYX and ADRIAMYCIN, thus demonstrating that the non-pegylated doxorubicin liposomes of the present invention have lower toxicity.

Example III—In sub-acute toxicity study, similar patter of toxicity was observed in both the CAELYX and composition of Example II groups whereas ADRIAMYCIN showed toxicity.

Example IV—In pharmacokinetic study, composition of Example II and CAELYX showed comparable plasma half-life. The apparent volume of distribution is approximately equal to the total blood volume, which indicated low liposomal uptake by normal tissues and was similar to CAELYX. ADRIAMYCIN showed faster clearance rate and high volume of distribution indicating uptake of free doxorubicin in normal tissues.

Example V—In dog toxicity study, composition of Example II found to be better tolerated than ADRIAMYCIN.

Example VI—In tumor models of L1210 mouse leukemia and MCF-7 human breast tumor, composition of Example II was found to be efficacious.

Example VII—Maximum tolerated dose of the composition of Example II was found to be much higher than ADRIAMYCIN in tumor implanted mice.

Example VIII—Composition of Example II was found to be efficacious in nude athymic mice implanted with a multi-drug resistant, Pgp positive, human colon DLD1 tumor xenografts.

The above Examples clearly prove that the compositions of the present invention are very useful for reducing tumor growth. This involves parenterally administering a therapeutically effective amount of non-pegylated doxorubicin hydrochloride liposomes of the present invention. The non-pegylated doxorubicin hydrochloride liposomes have a prolonged circulation time, exhibit decreased toxicity and do not present "Hand-Foot Syndrome" issues and hence they are useful for reducing tumor growth.

The invention claimed is:

1. A process for manufacture of long circulating non-pegylated liposomes comprising:
    dissolving one or more phospholipids and one or more sterols in a solvent or mixture of solvents;
    wherein the one or more phospholipids is a saturated phosphatidylcholine selected from the group consisting of distearoyl phosphatidylcholine (DSPC), hydrogenated soya phosphatidyl-choline (HSPC) and mixtures thereof;
    removing the solvent or mixture of solvents and adding an aqueous hydration media to the phospholipids and sterols; or adding an aqueous hydration media to the phospholipids and sterols in the solution; and removing the solvent or mixture of solvents;
    wherein the aqueous hydration media consists essentially of ammonium sulfate and sucrose and the amount of the aqueous hydration media used is in the range of 10 to 35 ml for each mmole of the phospholipid present to form long circulating non-pegylated liposomes; and
    removing ammonium sulphate from extra liposomal hydration medium by dialysis using a sucrose-histidine buffer solution.

2. The process of claim 1 wherein the amount of aqueous hydration media used is 30 ml for each mmole of phospholipid in the lipid solution.

3. The process of manufacture of non-pegylated liposomes of claim 1 further comprising loading the liposomes with a therapeutic or diagnostic agent after removal of the ammonium sulphate from the extra liposomal hydration medium.

4. The process of claim 3, wherein the therapeutic agent is an antineoplastic agent.

5. The process of claim 4, wherein the antineoplastic agent is selected from the group consisting of Doxorubicin hydrochloride, Daunorubicin hydrochloride, and Epirubicin hydrochloride.

6. The process of claim 5, wherein the antineoplastic agent is Doxorubicin hydrochloride.

7. The process of claim 1, wherein the molar ratio of phospholipid to sterol is from about 1:0.1-1:2.

8. The process of claim 7, wherein the molar ratio of phospholipid to sterol is about 1:0.7.

9. The process of claim 1, wherein the concentration of ammonium sulfate in aqueous hydration media is not less than 125 mmoles/liter.

10. The process of claim 1, wherein the phospholipid has a minimum of sixteen carbons fatty acid chain.

11. The process of claim 1, wherein the phospholipid is distearoyl phosphatidylcholine (DSPC) and wherein the sterol is cholesterol.

12. The process of claim 1, wherein the non-pegylated liposomes are successively extruded through series of filters having pore sizes from 0.4 μm to 0.05 μm for sizing.

13. A liposome manufactured by the process of claim 1.

14. The liposome of claim 13, wherein the phospholipid comprises distearoyl phosphatidylcholine (DSPC) and the sterol comprises cholesterol.

15. The liposome of claim 13, wherein the non-pegylated liposome further comprises a therapeutic or diagnostic agent.

16. The liposome of claim 15, wherein said therapeutic agent comprises an antineoplastic agent.

17. The liposome of claim 16, wherein the antineoplastic agent is selected from the group consisting of Doxorubicin hydrochloride, Daunorubicin hydrochloride, and Epirubicin hydrochloride.

18. The liposome of claim 17, wherein the antineoplastic agent is Doxorubicin hydrochloride.

19. The liposome of claim 13, wherein the average size of liposome is 0.06 μm to 0.16 μm in diameter.

20. A process for manufacture of non-pegylated liposomes comprising:
    forming a lipid film by evaporating a solvent from a lipid solution comprising one or more phospholipids, a sterol, and a solvent; and
    hydrating the lipid film by adding an aqueous hydration media to form a non-pegylated liposomal composition;
    wherein the aqueous hydration media consists essentially of ammonium sulfate and sucrose and wherein the amount of aqueous hydration media used is in the range of 10 to 35 ml for each mmole of phospholipid present in the lipid solution; and removing ammonium sulphate from extra liposomal hydration medium using a sucrose-histidine buffer solution.

21. The process of claim 20 wherein the aqueous hydration media comprises greater than 125 mM ammonium sulfate and 100 mM to 500 mM sucrose.

22. The process of claim 20 wherein the aqueous hydration media comprises greater than 125 mM ammonium sulfate and 250 mM to 300 mM sucrose.

23. The process of claim 20 wherein the amount of histidine in the sucrose-histidine buffer is 1 mM to 100 mM.

24. The process of claim 20 wherein amount of histidine in the sucrose-histidine buffer is 8 to 12 mM.

25. The process of claim 20 wherein amount of histidine in the sucrose-histidine buffer is 10 mM.

26. The process of claim 6 wherein the long circulating non-pegylated liposomes made by the process of claim 6 containing doxorubicin hydrochloride have a blood circulation half life of at least 25 times longer than obtained with ADRIAMYCIN when tested in Swiss albino mice at equivalent doses of doxorubicin hydrochloride.

\* \* \* \* \*